United States Patent [19]

Schneider

[11] Patent Number: 4,906,751

[45] Date of Patent: Mar. 6, 1990

[54] MERCAPTOTRIAZINE DERIVATIVES AS LUBRICANT ADDITIVES

[75] Inventor: Rainer Schneider, Zwingenberg, Fed. Rep. of Germany

[73] Assignee: Ciba-Geigy Corporation, Ardsley, N.Y.

[21] Appl. No.: 268,143

[22] Filed: Nov. 7, 1988

[30] Foreign Application Priority Data

Nov. 19, 1987 [CH] Switzerland ............ 04507/87

[51] Int. Cl.$^4$ .................. C07D 251/02; C07D 251/38
[52] U.S. Cl. ......................... 544/213; 544/60; 544/113; 544/208; 544/209; 544/210; 544/211; 544/212; 544/216; 544/219; 544/58.6; 544/83; 252/11; 252/50; 252/51; 252/51.5 R
[58] Field of Search ............... 544/213, 219, 113, 60, 544/208, 209, 210, 211, 212, 216, 58.6, 83

[56] References Cited

U.S. PATENT DOCUMENTS

| 3,784,588 | 1/1974 | Miles ........................... | 544/194 |
| 4,204,060 | 5/1980 | Hoentjen et al. .............. | 544/218 |
| 4,247,692 | 1/1981 | Sinnige et al. ................ | 544/194 |

FOREIGN PATENT DOCUMENTS

| 943637 | 12/1963 | United Kingdom ............ | 544/218 |
| 973351 | 10/1964 | United Kingdom ............ | 544/218 |

OTHER PUBLICATIONS

Gahdi et al. Applied Catalysis, 3, 79–88 (1982).
Encyclopedia of Chemical Technology, vol. 14, 3rd Ed. pp. 488 and 492 (1980).

*Primary Examiner*—Mary C. Lee
*Assistant Examiner*—J. Richter
*Attorney, Agent, or Firm*—Luther A. R. Hall

[57] ABSTRACT

Compounds of the formula

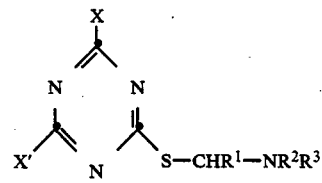

(I)

and of the formula

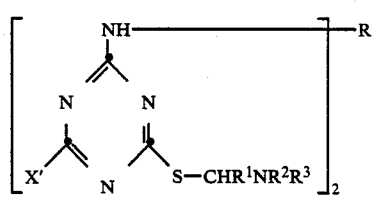

(II)

in which X and X' are, for example, —S—CHR$^1$, —NR$^2$R$^3$, —S—R$^3$, —NR$^2$R$^3$ or —OR$^3$, R$^1$ is, for example, —H, alkyl, cycloalkyl or phenyl, R$^2$ and R$^3$ are, for example, —H, alkyl, cycloalkyl or phenyl, or R$^2$ and R$^3$ together form a 3- to 7-membered heterocyclic ring, and R is alkylene, and compositions containing at least one compound of the formulae I and/or II and at least one lubricant, one hydraulic fluid or one metal working fluid, the compounds of the formula I and/or II being used as extreme pressure and wear-reducing additives.

8 Claims, No Drawings

MERCAPTOTRIAZINE DERIVATIVES AS LUBRICANT ADDITIVES

The present invention relates to novel mercaptotriazine compounds, compositions containing these and their use as lubricant additives.

The addition of additives to lubricants, such as mineral oils or synthetic or semi-synthetic lubricants, to improve the use properties is known. In particular, extreme pressure and wear-reducing additives are added to improve the wear protection properties of the lubricants. These additives should in turn be non-corrosive on the metal components to be lubricated.

For example, phosphorus- and sulfur-containing compounds from the dialkyl dithiophosphate series have been disclosed for the above intended use in German Offenlegungsschrift 2,921,620. In view of the use of catalysts in the exhaust systems of internal combustion engines, it is advisable to keep the phosphorus content of the lubricants as low as possible so that the catalyst is not deactivated (c.f. H. S. Gandhi et al. Applied Catalysis 3 (1982) 79-88).

Other known classes of compounds are the zinc dithiophosphates, which are capable of imparting a wear-reducing effect to lubricating oils (Kirk-Othmer, Encyclopedia of Chemical Technology, 3rd edition, Volume 14, pages 488 and 492).

Novel mercaptotriazine derivatives have now been found which are oil-soluble and free from both phosphorus and ash and are capable of meeting the required properties in respect of protection from frictional wear (antiwear), load-carrying capacity and protection of the metal components from corrosion.

The present invention accordingly relates to compounds of the formula

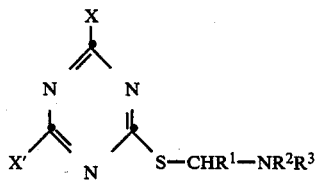

(I)

in which X and X' are identical or different and are —S—CHR$^1$—NR$^2$R$^3$, —S—R$^3$, —NR$^2$R$^3$ or —OR$^2$ and R$^1$ is —H, C$_1$–C$_{12}$alkyl, C$_5$–C$_{12}$cycloalkyl, 2-furyl, phenyl, naphthyl, C$_7$–C$_{11}$aralkyl or phenyl which is substituted by C$_1$–C$_4$alkyl, C$_1$–C$_4$alkoxy, C$_2$–C$_{24}$alkoxycarbonyl and/or nitro and R$^2$ and R$^3$ are identical or different and are —H, C$_1$–C$_{24}$alkyl, C$_1$–C$_{20}$alkyl which is substituted by hydroxyl and/or C$_1$–C$_4$alkyl, C$_1$–C$_{20}$alkyl which is interrupted by one or more —O—, —S— or —N— and/or contains oxo or thiono groups, C$_3$–C$_{24}$alkenyl, C$_3$–C$_{12}$alkoxyalkyl, C$_5$–C$_{12}$cycloalkyl, C$_7$–C$_{11}$aralkyl, phenyl which is unsubstituted or substituted by C$_1$–C$_{12}$alkyl, C$_1$–C$_4$alkoxy, C$_2$–C$_{24}$alkoxycarbonyl or nitro, naphthyl, 2-furyl, 2-furylmethyl or 2-(tetrahydrofuryl)-methyl, or in which R$^2$ and R$^3$, together with the nitrogen atom linking them, form a saturated or unsaturated 3- to 7-membered heterocyclic ring, or form a saturated or unsaturated 3- to 7-membered heterocyclic ring which contains other hetero atoms from the series comprising —O—, —N— and —S— and/or is substituted by oxo or thiono groups or fused by a benzo radical, or in which R$_2$ and R$_3$, together with the nitrogen atom linking them, form one of the heterocyclic rings mentioned, which is further substituted by C$_1$–C$_4$alkyl, C$_1$–C$_4$alkoxy, amino, methylamino, C$_1$–C$_4$aminoalkyl or nitro and compounds of the formula

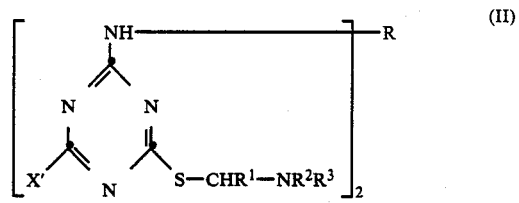

(II)

in which R is C$_1$–C$_{12}$alkylene, or C$_1$–C$_{12}$alkylene which is interrupted by —O—, —S— or —N— and/or contains oxo or thiono groups, or C$_6$–C$_{18}$cycloalkylene, C$_6$–C$_{18}$arylene, carbonyl or thiocarbonyl and X', R$^1$, R$^2$ and R$^3$ are as defined above.

R$^1$ can be alkyl with 1 to 12 carbon atoms and R$^2$ and R$^3$ can be alkyl with 1 to 24 carbon atoms.

Examples of these are methyl, ethyl, n-propyl, isopropyl, n-butyl, secbutyl, t-butyl, isoamyl, n-hexyl, 2-ethylbutyl, 1-methylpentyl, 1,3-dimethylbutyl, 1,1,3,3-tetramethylbutyl, isoheptyl, n-octyl, i-octyl, 2-ethylhexyl, 1-methylheptyl, 1,1,3-trimethylhexyl, n-decyl, 1-methylundecyl and n-dodecyl. Alkyl R$^2$ and R$^3$ can moreover also be, for example, tetradecyl, hexadecyl, octadecyl or eicosyl.

C$_5$–C$_2$Cycloalkyl R$^1$, R$^2$ and R$^3$ are to be understood as unsubstituted or C$_1$–C$_4$alkyl-substituted cycloalkyl rings. Examples of these are cyclopentyl, cyclohexyl, 4-methylcyclohexyl, cycloheptyl, cyclooctyl and cyclododecyl.

C$_7$–C$_{11}$Aralkyl R$^1$, R$^2$ and R$^3$ is, in particular, phenyl(C$_1$–C$_5$)alkyl or naphthylmethyl, and for example benzyl, α-methylbenzyl, α,α-dimethylbenzyl, 2-phenylethyl, 1-phenylethyl or 2-phenylpropyl.

Substituted phenyl R$^1$, R$^2$ and R$^3$ can be, for example, tolyl, xylyl, 4-t-butylphenyl, 3-methoxyphenyl, 4-propoxyphenyl, 3-nitrophenyl or 4-methyl-3-nitrophenyl, or phenyl which is substituted by alkoxycarbonyl, it being possible for alkoxy to be, for example, methoxy, ethoxy, isopropoxy or n-butoxy and 3-butoxycarbonylphenyl being mentioned as an example.

Alkenyl R$^2$ and R$^3$ can be, for example, allyl, methallyl, 1-pentenyl, dodecenyl or octadecenyl.

Alkoxyalkyl R$^2$ and R$^3$ can be, for example, 2-methoxyethyl, 2-isopropoxyethyl, 2-butoxyethyl or 2-octyloxyethyl.

If R$^2$ and R$^3$ together with the N atom form a heterocyclic ring, this is preferably 5- or 6-membered. If it also contains other hetero atoms, this is preferably an O or N atom. Examples are the pyrrolidine, piperidine, morpholine, thiomorpholine, piperazine, indole, tetrahydroquinoline or tetrahydroisoquinoline ring.

Alkylene R can be unbranched or branched alkylene, which can also be interrupted by —O—, —S— or —N—. Examples of these are di-, tri-, tetra-, hexa-, octa-, deca- or dodecamethylene; and 2,2,4- or 2,4,4-trimethylhexamethylene, 3-oxa-pentamethylene, 4-thia-heptamethylene or 4-(methylaza)-heptamethylene.

C$_6$–C$_{18}$Cycloalkylene R can be a saturated hydrocarbon group with two free valencies and at least one ring unit.

R here can also be cycloalkylene which is substituted by C$_1$–C$_4$alkyl. Examples are: C$_1$–C$_4$substituted cyclohexylene, such as methylcyclohexylene, or 1,4-decahydronaphthylene.

Furthermore, in the present case, cycloalkylene is also to be understood as alkylene-cycloalkylene-alkylene having 8 to 18 carbon atoms, advantageously alkylene-cyclohexylene-alkylene, and for example cyclohexylene-1,4-dimethylene, and also cycloalkylene-alkylene-cycloalkylene having 13 to 18 carbon atoms, advantageously cyclohexylene-alkylene-cyclohexylene, and for example dicyclohexylene-methane-4,4-diyl, and finally alkylidene-dicycloalkylene having 14 to 18 carbon atoms, advantageously alkylidene-dicyclohexylene, and for example isopropylidenedicyclohexylene.

Arylene R having 6 to 18 carbon atoms can be an unsubstituted or substituted aromatic group. Arylene R advantageously contains 6 to 10 carbon atoms and is phenylene, which is unsubstituted or substituted by $C_1$–$C_4$-alkyl. R is, for example, 1,2-phenylene, 1,3-phenylene or 1,4-phenylene. Arylene also includes in the present case biphenylene or naphthylene, which are unsubstituted or substituted by $C_1$–$C_4$alkyl. Examples of these which may be mentioned are 1,4-naphthylene, 4,4'-diphenylene, diphenyl-methane-4,4'-diyl and (diphenyl oxide)-4,4'-diyl.

The sum of the C atoms contained in the radicals $R^1$, $R^2$, $R^3$ and R is preferably more than 10, in particular more than 14. These radicals contribute towards the solubility in oil.

Preferred compounds of the formula I or II are those in which $R^1$ is hydrogen.

Compounds which are advantageous according to the invention have the formula I in which $R^1$ is —H, X is —$NR^{2'}R^{3'}$ or —S—$CH_2$—$NR^2R^3$, X' is —S—$CH_2$—$NR^2R^3$, $R^2$ and $R^3$ independently of one another are —H, $C_1$–$C_{20}$alkyl, $C_3$–$C_{24}$alkenyl, cyclohexyl, phenyl, phenyl which is substituted by $C_1$–$C_{12}$alkyl or $C_2$–$C_{24}$alkoxycarbonyl, $C_7$–$C_{11}$aralkyl or 3-methoxy-$C_1$–$C_4$alkyl and $R^{2'}$ and $R^{3'}$ are identical or different and are —H, $C_1$–$C_8$alkyl, $C_1$–$C_4$alkyl which is substituted by hydroxyl, phenyl or phenyl which is substituted by $C_1$–$C_4$alkyl, or $R^{2'}$ and $R^{3'}$, together with the nitrogen atom linking them, form a saturated 6-membered heterocyclic ring, which may contain an oxygen atom.

Compounds of the formula II in which $R^1$ is —H, X' is —S—$CH_2NR^2R^3$ and $R^2$ and $R^3$ independently of one another are —H, $C_1$–$C_{20}$alkyl, $C_3$–$C_{24}$alkenyl, cyclohexyl, phenyl, phenyl which is substituted by $C_1$–$C_{12}$alkyl or $C_2$–$C_{24}$alkoxycarbonyl, $C_7$–$C_{11}$aralkyl or 2- or 3-methoxy-$C_1$–$C_4$alkyl and R is $C_1$–$C_{12}$alkylene are advantageous.

Compounds of the formula I in which X is $NR^{2'}R^{3'}$ or —S—$CH_2$—$NR^2R^3$, X' is —S—$CH_2$—$R^2R^3$, $R^{2'}$ and $R^{3'}$ are identical or different and are —H, $C_1$–$C_4$alkyl, preferably methyl, $C_1$–$C_4$alkyl which is substituted by hydroxyl, preferably 2-hydroxyethyl, or phenyl, or $R^{2'}$ and $R^{3'}$, together with the N atom linking them, are morpholino and $R^2$ and $R^3$ are identical and are —H, $C_1$–$C_{12}$alkyl, $C_1$–$C_4$alkyl which is substituted by hydroxyl, phehyl or cyclohexyl, or $R^2$ and $R^3$, together with the N atom linking them, are morpholino, are preferred.

Preferred compounds of the formula II are those in which X' is —S—$CH_2$—$NR^2R^3$, $R^1$ is —H and $R^2$ and $R^3$ are identical and are —H, $C_1$–$C_{12}$alkyl, $C_1$–$C_4$alkyl which is substituted by hydroxyl, phenyl or cyclohexyl, or $R^2$ and $R^3$, together with the N atom linking them, are morpholino.

Further compounds which are likewise preferred are those of the formula I in which X and X' are —S—$CH_2$—$NR^2R^3$ and $R^2$ and $R^3$ are identical and are $C_4$–$C_8$alkyl, or compounds of the formula II in which X' is —S—$CH_2$—$NR^2R^3$, $R^2$ and $R^3$ are identical and are $C_4$–$C_8$alkyl, R is $C_nH_{2n}$ and n is a number from 1 to 6.

Compounds which are particularly preferred according to the present invention are those of the formula

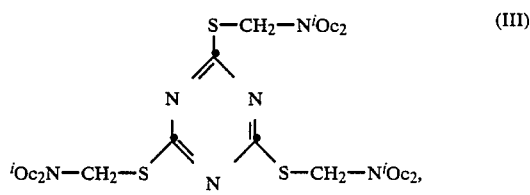

(III)

and

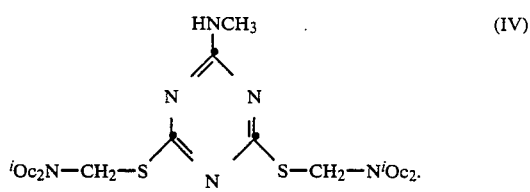

(IV)

In the present application, $^iOc$ is 2-ethylhexyl.

Examples of preferred compounds according to the invention are: 2-amino-4,6-bis-(di-2-ethylhexylamino-methyl-mercapto)-1,3,5-triazine, 2-morpholino-4,6-bis-(di-2-ethylhexylamino-methyl-mercapto)-1,3,5-triazine, 2-phenylamino-4,6-bis-(di-2-ethylhexylamino-methyl-mercapto)-1,3,5-triazine, 2-dihydroxyethylamino-4,6-bis-(di-2-ethylhexylamino-methyl-mercapto)-1,3,5-triazine, 2-methylamino-4,6-bis-(di-2-ethylhexylamino-methyl-mercapto)-1,3,5-triazine, 2-methylamino-4,6-bis-(di-n-butylamino-methyl-mercapto)-1,3,5-triazine, 2-methylamino-4,6-bis-(di-isobutylamino-methyl-mercapto)-1,3,5-triazine, 2-phenylamino-4,6-bis-(di-isobutylamino-methyl-mercapto)-1,3,5-triazine, 2-morpholino-4,6-bis-(di-isobutylamino-methyl-mercapto)-1,3,5-triazine, 2,4,6-tris-(di-isobutylamino-methyl-mercapto)-1,3,5-triazine, 2,4,6-tris-(di-2-ethylhexylamino-methyl-mercapto)-1,3,5-triazine, N,N'-bis-[4,6-bis(di-2-ethylhexylamino-methyl-mercapto)-1,3,5-triazin-2-yl]-hexamethylene-1,6-diamine, N,N'-bis-[4,6-bis(di-n-butylamino-methyl-mercapto)-1,3,5-triazin-2-yl]-hexamethylene-1,6-diamine and N,N'-bis-[4,6-bis(di-isobutylamino-methyl-mercapto)-1,3,5-triazin-2-yl]-hexamethylene-1,6-diamine.

The compounds of the formulae I and II can be prepared in a manner which is known per se.

An example which may be mentioned is a preparation process according to which a mercaptotriazine is reacted wtih the chosen amine and formaldehyde in the amount equivalent to the mercapto groups to be substituted. When the reaction has taken place, the volatile constituents can be distilled off in vacuo at about 100° C. and the end product can be obtained in a high purity and yield, if necessary after a clarification by filtration operation.

Various reaction paths for reaction of one of the maximum of three mercapto groups are shown by way of example in the equation given below. The remaining mercapto groups can be substituted by the desired radicals in succession in an analogous manner.

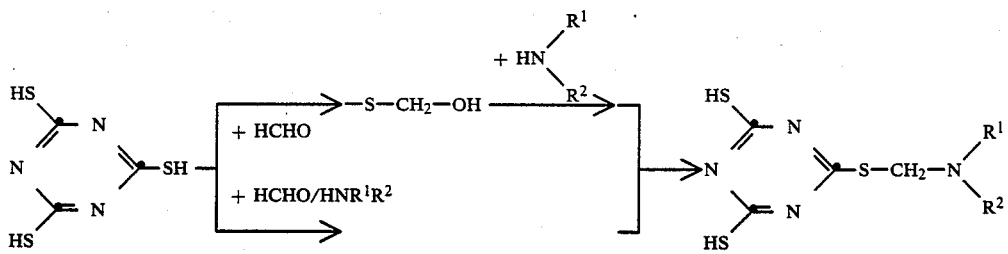

The mercaptotriazine derivatives according to the invention are accordingly prepared by a Mannich reaction from the corresponding mercaptotriazines with formaldehyde and an amine in a procedure which is customary per se.

Furthermore, in another preparation process, by the reaction which is known per se on cyanuric chloride (1,3,5-trichloro-2,4,6-triazine) at about 0° C., room temperature and elevated temperature, one chlorine atom can in each case be replaced by the desired group according to the present invention. For example, compounds of the formula II can be converted into the corresponding N,N'-bis[1,3,5-triazin-2-yl]alkylenediamine by reaction of 2 mol of cyanuric chloride with one mol of a divalent compound of the formula —NH—R—NH—.

The remaining chlorine groups can then be replaced by the desired radicals, for example by —SH groups, and this can be followed by the Mannich reaction described.

The compounds of the formula I and formula II and in particular the compounds mentioned as preferred are suitable as novel and useful wear protection and extreme pressure additives for so-called functional fluids, which include, for example, lubricants, such as lubricating oils and greases, hydraulic fluids and metal working fluids in the broadest sense.

The invention thus furthermore also relates to compositions containing at least one functional fluid in the sense described and at least one compound of the formula I and/or II.

The compounds described as advantageous or preferred according to the present invention lead accordingly to advantageous or preferred compositions when used in so-called functional fluids.

The addition of the compounds according to the invention to, for example, lubricants leads to an improvement in the general use properties, in particular the extreme pressure and anti-wear properties.

An improvement in the general use properties is also achieved in the same sense in hydraulic fluids and metal working fluids.

Since the compounds contain no phosphorus, they are particularly suitable for engine oils used in internal combustion engines with exhaust gas purification since damage to the catalyst downstream of the engine can be avoided.

Surprisingly, very good results are also achieved in the FZG test (Forschungsstelle Zahnrader Getriebe/TU Munich, DIN standard 51,354). This means that the compounds according to the invention have an outstanding performance in gear oils.

This is all the more surprising since the compounds are phosphorus-free, and sulfur-containing compounds are often said to have considerably poorer properties than the phosphorus-containing compounds in the FZG test.

The present invention therefore furthermore relates to the use of compounds of the formulae I and II, and preferably of the formulae III or IV, as extreme pressure and wear-reducing additives to lubricants, as additives to hydraulic fluids and as additives to metal working fluids.

The compounds of the formulae I and II are advantageously added to the lubricants, hydraulic fluids or metal working fluids in an amount of 0.05 to 5% by weight, preferably in an amount of 0.1 to 3% by weight, based on the total weight of the lubricants, hydraulic fluids or metal working fluids.

The lubricants, hydraulic fluids and metal working fluids in question are familiar to the expert and are described, for example, in "Schmiermittel Taschenbuch (Lubricants Handbook)" (Huethig Verlag, Heidelberg, 1974) and in "Ullmanns Encyclopadie der technischen Chemie (Ullmann's Encyclopaedia of Industrial Chemistry)" Volume 13, pages 85–94 (Verlag Chemie, Weinheim, 1977), or by D. Klamann in "Schmierstoffe und verwandte Produkte (Lubricants and Related Products)" Verlag Chemie, Weinheim (1982).

The lubricant can be, for example, an oil based on a mineral oil or a synthetic oil or a mixture of mineral oil and synthetic oil or a grease. The term mineral oil includes all mineral oils for lubricating purposes, such as mineral oils based on hydrocarbons. Synthetic oils can be, for example, aliphatic or aromatic carboxylic esters, polymeric esters, polyalkylene oxides, phosphoric acid esters, poly-α-olefins, silicones, glycols, polyglycols or polyalkylene glycols.

The lubricants or hydraulic fluids can additionally contain other additives which are added to improve the basic properties of lubricants or generally of "functional fluids" still further; these include anti-oxidants, metal passivators, rust inhibitors, agents for improving the viscosity index, agents for reducing the pour point, dispersing agents, detergents, other extreme pressure additives and other wear protection additives.

EXAMPLES OF PHENOLIC ANTIOXIDANTS

1. Alkylated monophenols
2,6-Di-tert-butyl-4-methylphenol, 2,6-di-tert-butylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-di-cyclopentyl-4-methylphenol, 2-(α-methylcyclohexyl)-4,6-dimethylphenol, 2,6-di-octadecyl-4-methylphenol, 2,4,6-tricyclohexylphenol, 2,6-di-tert-butyl-4-methoxymethylphenol and o-tert-butylphenol.

2. Alkylated hydroquinones
2,6-Di-tert-butyl-4-methoxyphenol, 2,5-di-tert-butylhydroquinone, 2,5-di-tert-amyl-hydroquinone and 2,6-diphenyl-4-octadecyloxyphenol.

3. Hydroxylated thiodiphenyl ethers 2,2'-Thio-bis-(6-tert-butyl-4-methylphenol), 2,2'-thio-bis-(4-octyl-phenol), 4,4'-thio-bis-(6-tert-butyl-3-methylphenol) and 4,4'-thio-bis-(6-tert-butyl-2-methylphenol).

4. Alkylidene-bisphenols 2,2'-Methylene-bis-(6-tert-butyl-4-methylphenol), 2,2'-methylene-bis-(6-tert-butyl-4-ethylphenol), 2,2'-methylene-bis-[4-methyl-6-(α-methylcyclohexyl)-phenol], 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4-iso-butylphenol), 2,2'-methylene-bis-[6-(α-methylbenzyl)-4-nonylphenol], 2,2'-methylene-bis-[6-(α, -dimethyl-benzyl)-4-nonylphenol], 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)-butane, 2,6-di-(3-tert-butyl-5-methyl-2-hydroxy-benzyl)-4-methylphenol, 1,1,3-tris-(5-tert-butyl-4-hydroxy-2-methylphenyl)-3-n-dodecyl-mercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene and bis-[2-(3'-tert-butyl-2'-hydroxy-5'-methylbenzyl)-6-tert-butyl-4-methyl-phenyl]terephthalate.

5. Benzyl compounds 1,3,5-tri-(3,5-di-tert-butyl-4-hydroxybenzyl)-2,4,6-trimethylbenzene, bis-(3,5-di-tert-butyl-4-hydroxybenzyl) sulfide, isooctyl 3,5-di-tert-butyl-4-hydroxybenzyl-mercaptoacetate, bis-(4-tert-butyl-3-hydroxy-2,6-dimethylbenzyl)-dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzyl-phosphonate and the calcium salt of monoethyl 3,5-di-tert-butyl-4-hydroxybenzyl-phosphonate.

6. Acylaminophenols

4-Hydroxy-laurylanilide, 4-hydroxy-stearylanilide, 2,4-bis-octylmercapto-6-(3,5-di-tert-butyl-4-hydroxyanilino)-s-triazine and octyl N-(3,5-di-tert-butyl-4-hydroxyphenyl)-carbamate.

7. Esters of β-(3,5-di-tert-butyl-4-hydroxyphenyl)-propionic acid with mono- or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol and bis-hydroxyethyl-oxalic acid diamide.

8. Esters of β-(5-tert-butyl-4-hydroxy-3-methylphenyl)-propionic acid with mono- or polyhydric alcohols, for example with methanol, diethylene glycol, octadecanol, triethylene glycol, 1,6-hexanediol, pentaerythritol, neopentylglycol, tris-hydroxyethyl isocyanurate, thiodiethylene glycol and di-hydroxyethyl-oxalic acid diamide.

9. Amides of β-(3,5-di-tert-butyl-4-hydroxyphenyl)-propionic acid, for example N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine and N,N'-bis-(3,5-di-tert-butyl-4-hydroxyphenylpropionyl)-hydrazine.

Examples of aminic antioxidants

N,N'-Di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-hetyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulphonamido)-diphenylamine, N,N'-dimethyl-N,N'-di-sec-butyl-p-phenylene-diamine, diphenylamine, N-allyl-diphenylamine, 4-isopropoxy-diphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)-amine, 2,6-di-tert-butyl-4-dimethyl-aminomethyl-phenol, 2,4'-diamino-diphenylmethane, 4,4'-diamino-diphenylmethane, N,N,N',N'-tetramethyl-4,4'-diamino-diphenylmethane, 1,2-di-[(2-methyl-phenyl)-amino]-ethane, 1,2-di-(phenylamino)-propane, (o-tolyl)-biguanide, di-[4-(1',3'-dimethyl-butyl)-phenyl]amine, tert-octylated N-phenyl-1-naphthylamine, a mixture of mono- and dialkylated tert-butyl-/tert-octyldiphenylamines, 2,3-dihydro-3,3-dimethyl-4H-1,4-benzothiazine, phenothiazine and N-allylphenothiazine.

Examples of other antioxidants

Aliphatic or aromatic phosphites, esters of thiodipropionic acid or of thiodiacetic acid, or salts of dithiocarbamic or dithiophosphoric acid.

Examples of metal passivators are: for copper, for example: triazoles, benzotriazoles and derivatives thereof, 2-mercaptobenzothiazole, 5,5'-methylenebisbenzotriazole, 4,5,6,7-tetrahydrobenzotriazole, 2,5-dimercaptothiadiazole, salicylidene-propyl-enediamine and salts of salicylaminoguanidine.

Examples of rust inhibitors are:

(a) Organic acids and their esters, metal salts and anhydrides, for example: N-oleoyl-sarcosine, sorbitan monooleate, lead naphthenate, dodecenylsuccinic anhydride, alkenylsuccinic acid half-esters and 4-nonylphenoxyacetic acid.

(b) Nitrogen-containing compounds, for example:
  I. Primary, secondary or tertiary aliphatic or cycloaliphatic amines and amine salts of organic and inorganic acids, for example oil-soluble alkylammonium carboxylates.
  II. Heterocyclic compounds, for example: substituted imidazolines and oxazolines.

(c) Phosphorus-containing compounds, for example: amine salts of phosphoric acid partial esters.

(d) Sulfur-containing compounds, for example: barium dinonylnaphthalene-sulfonates and calcium petroleum-sulfonates.

Examples of agents which improve the viscosity index are: polyacrylates, polymethacrylates, vinylpyrrolidone/methacrylate copolymers, polyvinylpyrrolidones, polybutenes, olefin copolymers, styrene/acrylate copolymers and polyethers.

Examples of agents which reduce the pour point are: polymethacrylate and alkylated naphthalene derivatives.

Examples of dispersing agents/surfactants are: polybutenylsuccinamides, polybutenylphosphonic acid derivatives and basic magnesium, calcium and barium sulfonates and phenolates.

Examples of wear protection additives are: compounds containing sulfur and/or phosphorus and/or halogen, such as sulfurized vegetable oils, zinc dialkyldithiophosphates, tritolyl phosphate, chlorinated paraffins, alkyl and aryl disulfides, triphenylphosphorothionates, diethanolaminomethyltolyltriazole and di(2-isooctyl)-aminomethyltolyltriazole.

The lubricant compositions according to the invention can also contain a co-lubricant system, for example by addition of customary amounts of solid lubricants, such as boron nitride, graphite, molybdenum disulfide, Teflon (tetrafluoroethylene) and the like.

The invention is illustrated in still more detail with the aid of the following examples.

The data in parts and percentages relate to the weight, unless stated otherwise.

Example 1

2-Methylamino-4,6-bis-(di-2-ethylhexylamino-methylmercapto)-1,3,5-triazine 2 mol (483 g) of di-2-ethylhexylamine and 162 g of a 37% formaldehyde solution are added to 1 mol (174 g) of 2-methylamino-4,6-bis-mercapto-1,3,5-triazine so that the temperature rises to about 70° C. This mixture is stirred for 1 hour at this temperature. The volatile constituents are then distilled off at 100° C. under <70 mbar and the end product is clarified by filtration. This gives the desired compound as a yellow viscous liquid of $n_D^{20}$ 1.5102.

Example 2

2,4,6-Tris-(di-2-ethylhexylamino-methyl-mercapto)-1,3,5-triazine 3 mol (724.5 g) of di-2-ethylhexylamine and 243 g of a 37% formaldehyde solution are added to 1 mol (177 g) of trismercaptotriazine so that the temperature rises to about 70° C. The mixture is stirred for 1 hour at this temperature. The volatile constituents are then distilled off at 100° C. under <70 mbar and the end product is clarified by filtration.

The desired compound is obtained as a yellow liquid of $n_D^{20}$ 1.5050.

Examples 3–11

The compounds shown in Table 1 are obtained analogously to Examples 1 and 2.

TABLE 1

| Example | | | $n_D^{20}$ |
|---|---|---|---|

Structure:

R²R³N—CH₂—S—[triazine ring with X substituent]—S—CH₂—NR²R³

| Example | NR²R³ | X | $n_D^{20}$ |
|---|---|---|---|
| 3 | N$^i$Oc₂ⁱ⁾ | —NH₂ | 1,5147 |
| 4 | = N$^i$Oc₂⁽¹⁾ | = —N(morpholino)O | 1,5221 |
| 5 | = N$^i$Oc₂⁽¹⁾ | = —NHPh | 1,5342 |
| 6 | = N$^i$Oc₂⁽¹⁾ | = —N(C₂H₄OH)₂ | 1,4974 |
| 7 | = —N$^n$Bu₂ | = —NHCH₃ | 1,5380 |
| 8 | = —N$^i$Bu₂ | = —NHCH₃ | 1,5262 |
| 9 | = —N$^i$Bu₂ | = —NHPh | 1,5540 |
| 10 | = —N$^i$Bu₂ | = —N(morpholino)O | Fp. 88° C. |
| 11 | = —N$^i$Bu₂ | = —S—CH₂—N$^i$Bu₂ | 1,5109 |

Structure (dimer):

[R²R³N—CH₂—S—triazine—S—CH₂—NR²R³ with HNC₃H₆—bridge]₂

| Example | NR²R³ | $n_D^{20}$ |
|---|---|---|
| 12 | N$^i$Oc₂⁽¹⁾ | 1,5159 |
| 13 | = N$^i$Bu₂ | 1,5302 |
| 14 | = N$^n$Bu₂ | 1,5152 |

⁽¹⁾$^i$Oc = 2-ethylhexyl

The following test methods are used for testing the synthetic compounds:

The following values are determined with the Shell four ball apparatus (IP 239/73 extreme pressure and wear lubricant test for oils and greases-four ball machine; ASTM-D 2783-81):

1. W.L.=Weld load in (N).
   This gives the load at which the 4 balls are welded together within 10 seconds.

2. W.S.D. = Wear scar diameter in (mm). The average wear diameter under a load of 40 kg for 1 hour. SSU 150 from Mobil is used as the base oil. The particular compound according to the invention is added in a concentration of 1% by weight.

The results are shown in Table 2.

TABLE 2

| Additives from Example | 1. W.L. (N) | 2. W.S.D. (mm) |
|---|---|---|
| Base oil | 1200 | 0,9 |
| Example 1 | 1600 | 0,5 |
| Example 2 | 1800 | 0,7 |
| Example 3 | 1600 | 0,5 |
| Example 4 | 1600 | 0,5 |
| Example 5 | 1800 | 0,55 |
| Example 8 | 1800 | 0,55 |
| Example 9 | 1600 | 0,55 |
| Example 11 | 1800 | 0,65 |
| Example 13 | 1600 | 0,55 |
| Example 14 | 1800 | 0,55 |

The results of the FZG test are shown in Table 3. (Forschungsstelle Zahnrader Getriebe/TU Munich, DIN standard 51,354).

A composition of 0.25% of the compound according to the invention in a base oil of Shell Catenex P 941 grade is tested here and the "failure load stage" (FLS) is determined. The values determined can be seen from Table 3.

TABLE 3

| Additives from Example | (0,25% in Catenex P 941) FLS |
|---|---|
| Base oil | 6 |
| Example 1 | >12 |
| Example 2 | >12 |
| Example 8 | 10 |

What is claimed is:

1. A compound of the formula

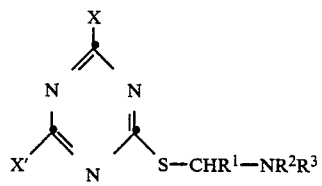

in which
X and X' are identical or different and are —S—CHR¹—NR²R³, —S—R³, —NR²R³ or —OR² and R¹ is —H, $C_1$-$C_{12}$-alkyl, $C_5$-$C_{12}$-cycloalkyl, 2-furyl, phenyl, naphthyl, $C_7$-$C_{11}$-aralkyl or phenyl substituted by $C_1$-$C_4$-alkyl, by $C_1$-$C_4$-alkoxy, by $C_2$-$C_{24}$-alkoxycarbonyl or by nitro or by mixtures thereof, and R² and R³ are identical or different and are —H, $C_1$-$C_{24}$-alkyl, $C_1$-$C_{20}$-alkyl substituted by hydroxyl, $C_1$-$C_{20}$-alkyl which is interrupted by one or more —O—, —S—, —N—, oxo or thiono groups or mixtures thereof, $C_3$-$C_{24}$-alkenyl, $C_3$-$C_{12}$-alkoxyalkyl, $C_5$-$C_{12}$-cycloalkyl, $C_7$-$C_{11}$-aralkyl, phenyl, phenyl substituted by $C_1$-$C_{12}$-alkyl, by $C_1$-$C_4$-alkoxy, by $C_2$-$C_{24}$-alkoxycarbonyl or by nitro; naphthyl, 2-furyl, 2-furylmethyl or 2-(tetrahydrofuryl)-methyl; or R² and R³, together with the nitrogen atom linking them, are pyrrolidino, piperidino, morpholino, thiomorpholino, piperazino, indolyl, tetrahydroquinolyl or tetrahydroisoquinolyl; or a compound of the formula

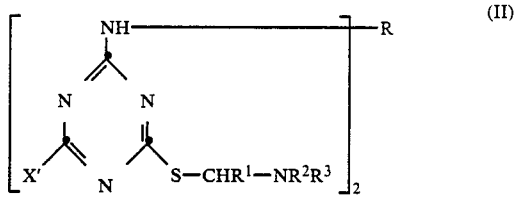

in which
R is $C_1$-$C_{12}$-alkylene, $C_1$-$C_{12}$-alkylene interrupted by one or more —O—, —S—, —N—, oxo or thiono groups or mixtures thereof; or $C_6$-$C_{18}$-cycloalkylene, $C_6$-$C_{18}$-arylene, carbonyl or thiocarbonyl, and X', R¹, R² and R³ are as defined above.

2. A compound of the formula I according to claim 1, in which X is NR²'R³' or —S—CH₂—NR²R³, X' is —S—CH₂—NR²R³, R²' and R³' are identical or different and are —H, $C_1$-$C_4$alkyl, $C_1$-$C_4$alkyl which is substituted by hydroxyl, or phenyl, or R²' and R³', together with the N atom linking them, are morpholino and R² and R³ are identical and are —H, $C_1$-$C_{12}$alkyl, $C_1$-$C_4$alkyl which is substituted by hydroxyl, phenyl or cyclohexyl, or R² and R³, together with the N atom linking them, are morpholino.

3. A compound of the formula I according to claim 1, in which R¹ is —H, X is —NR²'R³' or 13 S—CH₂—NR²R³, X' is —S—CH₂—NR²R³, R² and R³ independently of one another are —H, $C_1$-$C_{20}$alkyl, $C_3$-$C_{24}$alkenyl, cyclohexyl, phenyl, phenyl which is substituted by $C_1$-$C_{12}$alkyl or $C_2$-$C_{24}$alkoxy-carbonyl, $C_7$-$C_{11}$aralkyl, 2- or 3-methoxy-$C_1$-$C_4$alkyl and R²' and R³' are identical or different and are —H, $C_1$-$C_8$alkyl, $C_1$-$C_4$alkyl which is substituted by hydroxyl, phenyl or phenyl which is substituted by $C_1$-$C_4$alkyl, or R²' and R³', together with the nitrogen atom linking them, are morpholino.

4. A compound of the formula II according to claim 1, in which R¹ is —H, X' is —S—CH₂—NR²R³ and R² and R³ independently of one another are —H, $C_1$-$C_{20}$alkyl, $C_3$-$C_{24}$alkenyl, cyclohexyl, phenyl, phenyl which is substituted by $C_1$-$C_{12}$alkyl or $C_2$-$C_{24}$alkoxycarbonyl, $C_7$-$C_{11}$aralkyl, or 2- or 3-methoxy-$C_1$-$C_4$alkyl and R is $C_1$-$C_{12}$alkylene.

5. A compound according to claim 2 wherein R²' and R³' are methyl or 2-hydroxyethyl.

6. A compound of the formula II according to claim 1, in which X' is —S—CH₂NR²R³, R¹ is —H and R² and R³ are identical and are —H, $C_1$-$C_{12}$alkyl, $C_1$-$C_4$alkyl which is substituted by hydroxyl, phenyl or cyclohexyl, or R² and R³, together with the N atom linking them, are morpholino.

7. A compound of the formula I according to claim 1, in which X and X' are —S—CH₂—NR²R³ and R² and R³ are identical and are $C_4$-$C_8$alkyl, or a compound of the formula II according to claim 1, in which X' is —S—CH₂—NR²R³, R² and R³ are identical and are $C_4$-$C_8$alkyl, R is $C_nH_{2n}$ and n is a number from 1 to 6.

8. The compound according to claim 1, of the formula

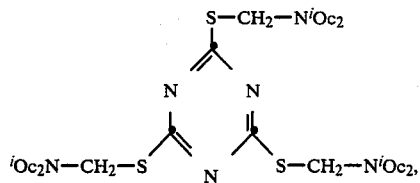 (III)
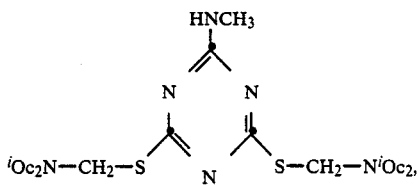 (IV)
in which $^i Oc$ is 2-ethylhexyl.
* * * * *